United States Patent [19]

Kopecko et al.

[11] Patent Number: 5,055,394
[45] Date of Patent: Oct. 8, 1991

[54] NUCLEIC ACID PROBE AND METHOD FOR THE RAPID DETECTION OF TYPHOID FEVER BACTERIA

[75] Inventors: Dennis J. Kopecko, Rockville; Louis S. Barson, Silver Spring; Fran A. Rubin, Bethesda, all of Md.

[73] Assignee: The United States of America as represented by the Secretary of the Army, Washington, D.C.

[21] Appl. No.: 877,077

[22] Filed: Jun. 23, 1986

Related U.S. Application Data

[63] Continuation-in-part of Ser. No. 541,760, Oct. 13, 1983, abandoned.

[51] Int. Cl.$^5$ .................. C12Q 1/68; C12Q 1/04; C12N 15/00
[52] U.S. Cl. .................. 435/6; 435/7.9; 435/34; 435/320.1; 435/879; 536/27; 436/501
[58] Field of Search .................. 435/6, 7, 34, 879, 320, 435/7.9, 320.1; 536/27

[56] References Cited

PUBLICATIONS

Snellings et al., Journal of Bacteriology, vol. 145, No. 2, pp. 1010–1017, (Feb. 1981).
Baron et al., in Genetic Engineering of Microorganisms for Chemicals (Ed. A. Hollander) Plenum Press N.Y. pp. 175–194 (1982).
Moseley et al., J. of Infect. Dis., vol. 142, No. 6, (Dec. 1980), pp. 892–898.

*Primary Examiner*—Esther L. Kepplinger
*Assistant Examiner*—Toni R. Scheiner
*Attorney, Agent, or Firm*—Werten F. W. Bellamy

[57] ABSTRACT

This invention relates to a nucleic acid probe and method for the rapid detection of typhoid fever bacteria by use of a nucleic acid hybridization probe, equivalent to the DNA region encoding the Vi antigen of enteric bacteria such as *Salmonella typhi*, *S. paratyphi* C, or *Citrobacter freundii*, in a nucleic acid hybridization reaction with a clinical specimen containing typhoid fever bacteria.

21 Claims, 1 Drawing Sheet

Restriction Endonuclease Digestion Map of the EcoR1-A fragment of the viaB gene region.

NUCLEIC ACID PROBE AND METHOD FOR THE RAPID DETECTION OF TYPHOID FEVER BACTERIA

CROSS REFERENCE

This application is a continuation-in-part of U. S. Pat. application Ser. No. 541,760, filed Oct. 13, 1983.

BACKGROUND OF THE INVENTION

1. Field of the Invention

All publications or patents mentioned in this specification are herein incorporated by reference.

This invention relates to a unique nucleic acid hybridization probe and method for the rapid detection of typhoid fever bacteria.

2. Prior Disclosure

Diarrheal diseases caused by enteric bacteria are still a major cause of illness and death worldwide, especially among infants and young children in developing nations. Also, these maladies are an important military problem in deployed soldiers. Although the incidence of diarrheal disease is highest in tropical countries, geography is not as important a factor as socioeconomic conditions; e.g. as manifested by drinking water purity, sewage disposal methods, and the availability of balanced diets. Some enteric diseases are short-lived, self-limiting and result in a mild gastroenteritis (e.g. certain Salmonella serotypes). In contrast, typhoid fever, caused by *Salmonella typhi*, is a prolonged, generalized, and usually serious infection of humans of all age groups. Similar enteric diseases are caused by related bacteria such as *Salmonella paratyphi* A, B, and C and by other Salmonella serotypes.

All strains of *Salmonella typhi* and *S. paratyphi* C, as well as a few atypical but genetically related Citrobacter and Salmonella strains, are capable of synthesizing a capsular antigen termed Vi for virulence (Edwards, P. R., and W. H. Ewing, 1972, Identification of *Enterobacteriaceae*, 3rd Edition pages 146–207, Burgess Publishing Company, Minneapolis). This galactosamine uronic acid polymer (i.e. the Vi antigen) has been associated with the virulence of *S. typhi* (Felix, A., S. S. Bhatnagar, and R. M. Pitt, 1934, Observations on the Properties of the Vi Antigen of *B. typhosus*, Br. J. Exp. Pathol. 15:346–354; and Heyns, K., G. Kiessling, W. Lindenberg, H. Paulsen, and M. E. Webster, 1959, d-Galaktosaminuronsaure (2-Amino-2-desoxy-D-galakturonsaure) als Baustein des Vi-Antigens, Chem. Ber. 92:2435–2437). Two separate chromosomal loci necessary for Vi antigen expression, viaA and viaB, have been identified in genetic studies of *S. typhi* (Johnson, E. M., B. Krauskopf, and L. S. Baron, 1965, Genetic mapping of Vi and somatic antigenic determinants in Salmonella, J. Bacteriol. 90:302–308; and Johnson, E. M. B., B. Krauskopf, and L. S. Baron, 1966, Genetic analysis of the viaA-his chromosomal region in Salmonella, J. Bacteriol. 92:1457–1463). The viaB region appears to encode the structural genes for this antigen (Johnson, E. M., B. Krauskopf, and L. S. Baron, 1965, Genetic mapping of Vi and somatic antigenic determinants in Salmonella, J. Bacteriol. 90:302–308). Analogous and presumably allelic chromosomal sites have been identified in S. paratyphi C (Snellings, N. J., E. M. Johnson, and L. S. Baron, 1977, Genetic basis of Vi antigen expression in *Salmonella paratyphi* C. J. Bacteriol. 131:57–62) and in some strains of *Citrobacter freundii* (Snellings, N. J., E. M. Johnson, D. J. Kopecko, H. H. Collins, and L. S. Baron, 1981, Genetic regulation of variable Vi antigen expression in a strain of *Citrobacter freundii*, J. Bacteriol. 145:1010–1017). Although the expression of the Vi antigen is relatively stable in *S. typhi*, Vi-positive Citrobacter strains exhibit a rapid, reversible transition between forms that express the Vi antigen and forms that appear not to express it, referred to as non-Vi or W forms (Baron, L. S., D. J. Kopecko, S. M. McCowen, N. J. Snellings, E. M. Johnson, W. C. Reid, and C. A. Life, 1982, Genetic and molecular studies on the regulation of a typical citrate utilization and variable Vi antigen expression in enteric bacteria, pages 175–194, In Hollaender (Editor), *Genetic Engineering of Microorganisms For Chemicals*, Plenum Press, NY; and Snellings, N. J., E. M. Johnson, D. J. Kopecko, H H Collins, and L. S. Baron, 1981, Genetic regulation of variable Vi antigen expression in a strain of *Citrobacter freundii*, J. Bacteriol. 3 145 1010–1017).

Proper chemotherapeutic treatment of typhoid or related enteric fever disease in many cases is only instituted following the proper identification of the causative agent. The standard biochemical and serological identification of enteric bacteria from fecal or blood specimens generally requires 24 to 48 hours even with the most up-to-date clinical microbiology facilities. The absence of these facilities in areas of military troop deployment and in underdeveloped countries prevents the proper epidemiological identification of diseases and the administration of appropriate chemotherapeutic regimens. A rapid method, which could be utilized in remote, ill-equipped areas, for the identification of specific enteric bacteria would be of obvious benefit to mankind. Several scientific groups have developed deoxyribonucleic acid (i.e. DNA) hybridization techniques, disclosed in U. S. Pat. Nos. 4,358,535 (Falkow, et al.) and 4,139,346 (Rabbani), and specific immunological procedures for the rapid identification of bacteria viruses and other organisms in culture specimens. Thus, there are several basic concepts available around which one can design a rapid diagnostic detection tool. Notwithstanding these readily available data, it takes considerable ingenuity to develop a bacterial identification assay that is differentially specific, rapid and inexpensive, and which can he conducted in remote areas with little equipment. For these reasons, relatively few rapid diagnostic assays are broadly applicable.

DNA Hybridization Procedures

The bacterial chromosome is a double-stranded DNA molecule in which one DNA strand is chemically complementary and hydrogen-bonded to the other DNA strand. These strands can be separated and reannealed, to form a hybrid, with single DNA strands of another type. Nucleic acid hybridization is a term used to define the chemical reaction that occurs between two complementary and homologous DNA strands or between DNA and ribonucleic acid (i.e. RNA) as described in U. S. Pat. No. 4,358 535.

This biochemical methodology, which was developed over the past 20 years, has recently been applied to the detection of pathogenic bacteria in clinical specimens (Moseley, S. L., et al., J. Infect. Dis., 1982, 145:863–869). This hybridization procedure requires: (1) a nucleic acid probe sequence that will specifically hybridize with a particular bacterial DNA sequence; and (2) clinical specimens to analyze for the particular pathogenic bacteria. The procedure involves: (1) preparing a labelled (i.e. detectable) nucleic acid probe; (2) inoculating the clinical specimens on nitrocellulose filters or other appropriate support material; (3) preparing the clinical specimens on the filter for hybridization; (4) conducting the hybridization reaction between the nucleic acid probe and the clinical specimen fixed on the support material; and, finally (5) detection of any specimens that bound the labelled probe DNA. These general steps are outlined in Table 1.

The article (J. Infect. Dis. 145:863–869) referenced above employed radiolabeled probe DNA and used autoradiography to detect the reacted clinical specimens. Although this technique is very useful in the identification of certain pathogenic organisms, identification still requires 24 or more hours. There are presently available alternate methods to detect hybridized probe DNA; (e.g. one commercially available method employs a DNA probe labeled with biotinylated nucleotides which can be detected in a few hours. This methodology suggests that identification of S. typhi may be obtained within several hours, using a biotinylated DNA probe in conjunction with hybridization procedures.

Basic Genetic Studies of the Vi Antigen

The virulence (Vi) antigen is a capsular monosaccharide polymer of galactosamine uronic acid and it is produced by all strains of Salmonella typhi and Salmonella paratyphi C and by a few strains of Citrobacter freundii. This antigen appears to be essential for the intracellular survival of the bacterial host and, hence, it is an important virulence property. Previous genetic studies have been revealed that this antigen is encoded by two widely separated chromosomal loci designated viaA and viaB that are situated at analogous positions in the chromosomes of S. typhi, S. paratyphi C, and C. freundii. The ViaA locus is located near his (chromosomal minute 44) and the ViaB region is situated near mel (92 minutes) on the chromosome. Certain strains of Citrobacter freundii exhibit an unusual, frequent, reversible expression of the Vi antigen (i.e. these cells undergo a reversible transition between full Vi antigen expression and no Vi antigen expression). Each cell is, thus, reversibly able to generate the alternate type. The basic genetic importance of this "expression switch" called for further study. Further genetic studies have demonstrated that the ViaB locus encodes the structural genes determining Vi antigen expression as well as the associated "expression switch" (Baron, L. S., et al., 1982, pages 175–194, in Genetic Engineering of Microorganisms for Chemicals, (Editor, A. Hollaender), Plenum Press, NY). These basic genetic studies, as described in the L. S. Baron, et al. article, were aimed only at studying the unusual expression switch and not at isolating a DNA probe for diagnostic detection. As mentioned previously, Vi antigen expression in enteric bacteria is controlled by two widely separated and distinct genetic regions termed viaA and viaB. In addition, the viaA gene region is normally present in some enteric organisms that do not synthesize a Vi antigen, e.g. E. coli and Salmonella typhimurium. DNA from this genetic region would not serve as a specific probe for Vi-expressing organisms. However, this point is not deemed obvious and is only known by a few scientists. Although one might guess that the viaB gene region might serve as a specific probe, the only way to be sure is to clone the appropriate DNA fragment and test it for specificity in DNA hybridization reactions, which involves extensive experimentation of the type disclosed by herein.

SUMMARY OF THE INVENTION

This invention is directed to a method for the rapid detection of typhoid fever bacteria by use of a unique nucleic acid hybridization probe, equivalent to the DNA region encoding the Vi antigen of enteric bacteria such as Salmonella typhi, Salmonella paratyphi C, or Citrobacter freundii, in a nucleic acid hybridization reaction with a clinical specimen containing typhoid fever bacteria.

Another embodiment of this invention is directed to a nucleic acid probe, consisting of an 18 kilobase pair (kb; 1 megadalton equals 1.5 kb) nucleic acid segment, or any subset of these sequences) representing the viaB region of the Vi antigen encoding sequences, that can be used to detect diagnostically Salmonella typhi, the typhoid fever bacillus. All clinical isolates of Salmonella typhi are Vi-antigen-expressing and no other enteric bacterium is known to express the Vi antigen except very rare strains of Citrobacter freundii and strains of Salmonella paratyphi C, which are thought to be much less prevalent pathogens than S. typhi. Thus, reaction of a clinical specimen with a probe specific for the Vi antigen genes is highly diagnostic for typhoid fever bacilli.

We have identified a DNA sequence that could be used to facilitate the diagnostic identification of Salmonella typhi, the causative agent of typhoid fever. All virulent S. typhi strains encode a relatively unique capsular antigen termed the virulence (Vi) antigen. Two distinct genetic loci, viaA and viaB, are involved in the synthesis of this antigen. The structural genes, located at viaB, were considered as a possible specific DNA probe. The viaB locus, contained in a recombinant cosmid, was subcloned to various plasmid vectors for this purpose. Selected viaB-region DNA fragments were then analyzed for specificity in DNA colony hybridization reactions with more than 170 strains representing a variety of enteric bacteria. An 8.6-kilobase EcoRl fragment was highly specific for the viaB gene region and was considered a good hybridization probe. This DNA probe should prove useful in rapid diagnostic assays set up to detect S. typhi in mixed bacterial samples (e.g., stools) within a few hours of specimen collection.

BRIEF DESCRIPTION OF THE DRAWINGS

A more complete appreciation of the invention and many of the attendant advantages thereof will be readily obtained by reference to the following detailed description when considered in conjunction with FIGS. 1 and 2, wherein.

DETAILED DESCRIPTION OF THE INVENTION

Figure 1:
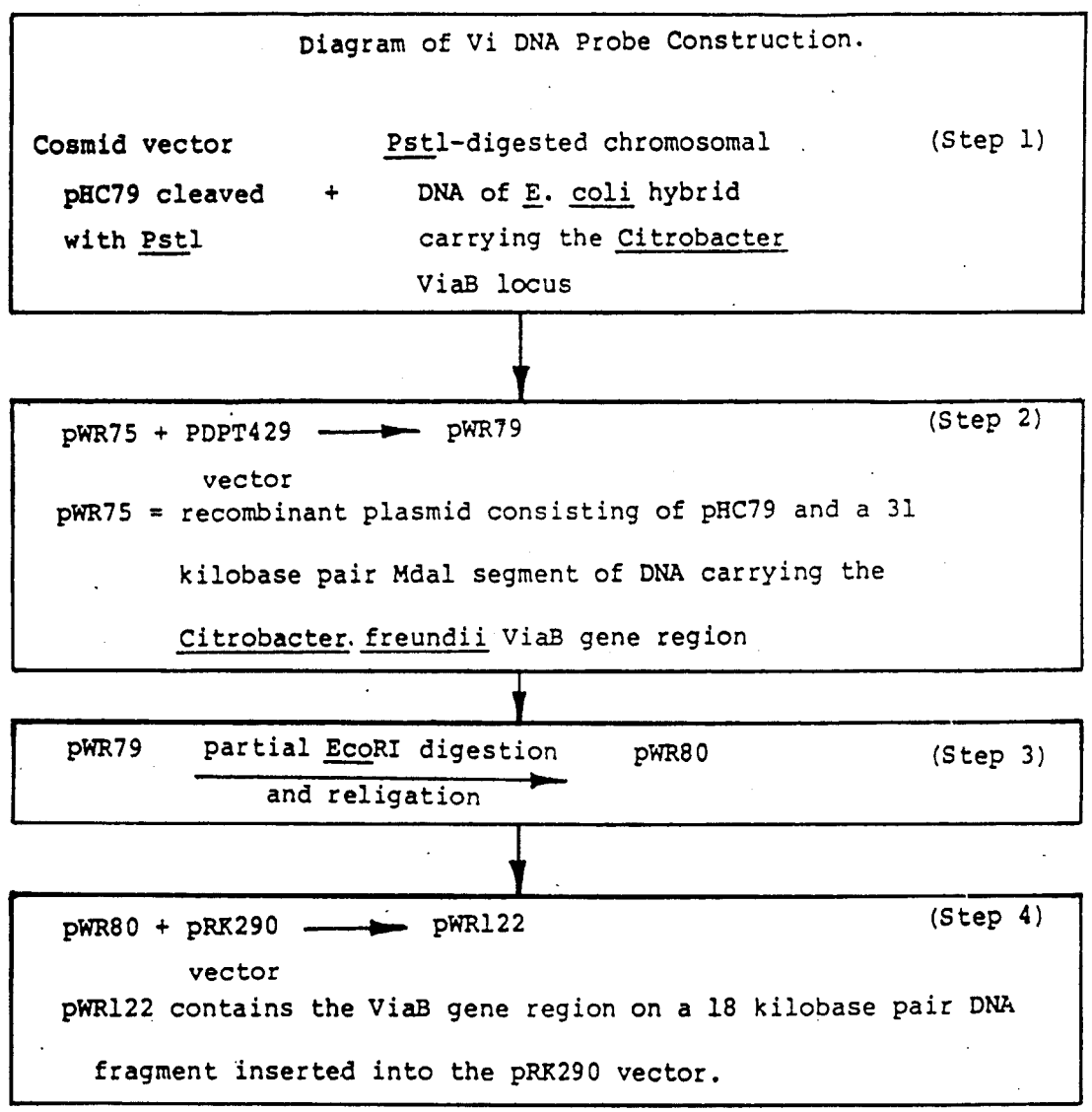
FIG. 1 illustrates Vi DNA probe construction.
Figure 2:
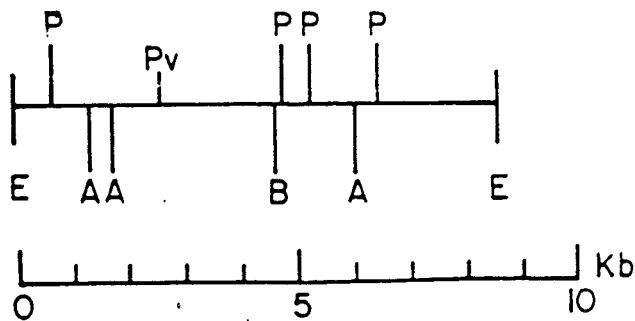
FIG. 2 illustrates the restriction endonuclease digestion map of the EcoRl-A fragment of the viaB region. The restriction endonuclease digestion sites are designated as follows: E, EcoRl; A, AvaI; B, BglII; P, PstI; and Pv, PvuII.

It is understood that the DNA probes described herein, for purposes of illustration, can h=converted to their corresponding RNA probes by well known techniques (e.g. the commercially available Riboprobe System TM.

Materials and Methods

Bacterial strains and plasmids. Bacterial strains and plasmids are listed in Tables 3 and 4. *S. typhi* WR4201 (ViaA+ViaB+) expresses the Vi antigen; previously constructed derivatives WR4205 (Johnson, E M., B. Krauskopf, and L. S. Baron, 1965, Genetic mapping of Vi and somatic antigenic determinants in Salmonella, J. Bacteriol. 90:302-308) and WR4226 (Snellings, N. J., E. M. Johnson, D. J. Kopecko, H. H. Collins, and L. S. Baron, 1981, Genetic regulation of variable Vi antigen expression in a strain of *Citrbacter freundii*, J. Bacteriol. 145:1010-1017) were used as DNA hybridization controls since they are ViaA−, ViaB+ and ViaA1+, ViaB−, respectively. *Escherichia coli* WR2376, a Vi-positive *E. coli* C600 recombinant carrying the viaB locus of *C freundii* WR7004 (Baron, L. S., et al., D. J. Kopecko, S. M. McCowen, N. J. Snellings, E. M. Johnson, W. C. Reid, and C. A. Life, 1982, Genetic and molecular studies on the regulation of atypical citrate utilization and variable Vi antigen expression in enteric bacteria, pages 175-194) was also used as a DNA hybridization control in some experiments. Salmonella strains from the Centers for Disease Control (CDC), Atlanta, GA, used to determine probe specificity included groups A, B, $C_1$, $C_2$, $C_3$, $D_1$, $D_2$, $E_1$, $E_2$, $E_3$, $E_4$, F, $G_1$, $G_2$, H, I, J, K, L, M, N, 0, P, Q, R, S, T, U, V, W, X, Y, Z, 51, 52, 53, 54, 55, 66, and 67. Additional bacterial strains were obtained from the collection at the Walter Reed Army Institute of Research (WRAIR), Washington, DC.

Media and culture conditions. Bacteria were grown at 37° C. on nutrient agar or in Penassay or brain heart infusion broth (Difco Laboratores, Detroit, MI). Antibiotics were used at the following final concentrations: kanamycin, 20 mirograms per ml; tetracycline, 10 mirograms per ml; chloramphenicol, 20 micrograms per ml; spectinomycin, 25 micrograms per ml; and ampicillin, 25 micrograms per ml.

Vi antigen expression. Vi antigen-expressing bacterial colonies on agar media were identified microscopically by oblique illumination (Snellings, N. J., E. M. Johnson, D. J. Kopecko, H. H. Collins, and L. S. Baron, 1981, Genetic regulation of variable Vi antigen expression in a strain *Citrobacter freundii*, J. Bacteriol. 145:1010-1017). Vi antigen-expressing forms are seen as dense, bright, orange-tinted colonies which are readily distinguishable from the dull, translucent colonies of non-Vi forms. Vi antigen expression was verified by slide agglutination with rabbit antiserum prepared against Vi-encapsulated *C. freundii* WR7004 cells. An additional test for Vi antigen expression involved the sensitivity of Vi antigen-expressing cells to Vi-specific typing phage. A drop of Vi phage was spotted on an area of a nutrient agar plate that was heavily swabbed with a bacterial culture. After overnight incubation at 37° C., cell lysis was observed in the spotted area only in the case of cells expressing the Vi antigen.

Isolation and manipulation of DNA. Bacterial cells were grown at 37° C. for 16 to 18 hours in Penassay broth. Plasmid DNA was isolated by a cleared lysis method with Triton X-100 detergent followed by plasmid purification on cesium chloride density gradients, (Kupersztoch, Y.M. and D.R. Helinski, 1973. A catenated DNA molecule as an intermediate in the replication of the resistance transfer factor R6K in *Escherichia coli*, Biochem. Biophys. Res. Commun. 54:1451-1459). Digestion of DNA with restriction endonucleases was carried out under the conditions specified by the vendor (New England Bio. Labs., Inc., Beverly, MA; International Biotechnologies, Inc., New Haven, CT). Plasmids and restriction endonuclease-generated DNA fragments were resolved and analyzed by horizontal gel electrophoresis (International Biotechnologies, Inc.) in 0.7 to 2.0% agarose (SeaKem; FMC Corp., Maine Colloids Div., Rockland, ME; International Biotechnologies, Inc.) prepared in TBE buffer (89 mM Tris, pH 8.3, 2.5 mM EDTA, 89 mM boric acid). We visualized DNA bands by staining the gel in 0.5 micrograms of aqueous ethidium bromide per ml and then illuminating it with a 300-nm UV light source (Fotodyne, New Berlin, WI).

Recombinant plasmids were constructed in vitro by ligation, with T4 DNA ligase, of endonuclease-linearized vector DNA to endonuclease-generated DNA fragments (New England Bio. Labs.) at 17° C. for 16 to 18 hours with the buffer described by Maniatis, et al. (1982, Molecular cloning. A laboratory manual, Cold Spring Harbor Laboratory, Cold Spring Harbor, NY). *E. coli* HB101 cells were prepared for transformation with plasmid DNA by the method of Kushner, (Kushner, S. R., 1978. An improved method for transformation of *Escherichia coli* with ColE1 derived plasmids, pages 17-23. In H. W. Boyer and S. Nicosia (edition), Genetic engineering, Elsevier/North-Holland Biomedical Press. Amsterdam).

Preparation of $^{32}$P-labeled DNA probes. To purify DNA fragments for use as probes in hybridization experiments, we digested plasmids with the selected restriction endonucleases and resolved the resulting fragments by agarose gel electrophoresis. After ethidium bromide staining of the gel, the appropriate DNA band was cut out and the DNA was electroeluted with (i) a concentrator (model 1750; ISCO, Lincoln, NE) or (ii) a dialysis membrane filled with the agarose slice and TE buffer (0.01 M Tris, pH 8.0, 0.001 M EDTA) with 0.1 ×TBE buffer surrounding the membrane (100 V for 2 hours followed by reversed current for 2 minutes), (Maniatis, T., E. F. Fritsch, and J. Sambrook, 1982, Molecular cloning. A laboratory manual. Cold Spring Harbor Laboratory, Cold Spring Harbor, NY). Fragments were further purified by another round of agarose gel electrophoresis followed by electroelution. Vi antigen gene locus fragments were radiolabeled in vitro by nick translation, (Rigby, P. W. J., M. Dieckmann C. Rhodes, and 4P. Berg, 1977. Labeling deoxyribonucleic acid to high specific activity in vitro by nick translation with DNA polymerase. I, J. Mol. Bio. 113:237-251) with a kit from New England Nuclear Corp., Boston, MA. (Alpha-$^{32}$P dCTP, 3,000 Ci/mmol). After 1 hour at 14° C., 6 microliters of 0.3 M EDTA was added to terminate the reaction. Unincorporated nucleotides were separated from labeled DNA by centrifugation through a 1-ml Sephadex G-50 column equilibrated and run with 0.2% sodium dodecyl sulfate (SDS)-0.1 M NaCl in TE 16 buffer. Specific activity of the probe was usually $2 \times 10^8$ cpm/microgram of probe DNA.

Filters for in situ colony hybridization. Pure bacterial cultures were grown overnight and transferred by toothpick to an 82-mm diameter nitrocellulose filter (BA 85; Schleicher & Schuyll, Inc., Keene, NH; HAHY 082 50; Millipore Corp., Bedford, MA) layered on MacConkey agar. Generally, 15 to 50 cultures were inoculated on each nitrocellulose filter. After 3 to 6 hours of incubation at 37° C., the filters were removed from the agar and the attached cells were lysed with 0.5 M NaOH and prepared by the method described by Moseley, et al., (Moseley, S. L., P. Echeverria, J. Seriwatana, C. Tirapat, W. Chaicumpa, T. Sakuldaipeara, and S. Falkow, 1982. Identification of enterotoxigenic *Escherichia coli* by colony hybridization using three enterotoxin gene probes, J. Infect. Dis. 145:863–669). These nitrocellulose filters were then transferred face up for one 1 minute each to a series of three paper filters each saturated with 1.0 M ammonium acetate and 0.02 M NaOH. After 10 minutes on a fourth change of the latter solution, nitrocellulose filters were air dried and the DNA was fixed by incubation at 70° C. for 2 hours in vacuo.

In addition to nitrocellulose, 541 paper (Whatman, Inc., Clifton, NJ) was used as a solid support for DNA hybridizations. The Whatman 541 papers were prepared by the method described by Maas, (Maas, R., 1983. An improved colony hybridization method with significantly increased sensitivity for detection of single genes, Plasmid 10:296–298). An 82-mm circular piece of Whatman 541 paper was placed over colonies that had been inoculated onto a nutrient agar plate and incubated at 37° C. overnight. After approximately 15 minutes, the Whatman 541 paper was peeled off and placed colony side up on a paper filter saturated with 0.5 M NaOH-1.5 M NaCl (lysing solution), steamed for 3 minutes, immersed in fresh lysing buffer for 1 minute, immersed in 1 M Tris (pH7)-2 M NaCl (neutralization solution) for 4 minutes, and air dried. Prehybridization of Whatman 541 paper is not necessary; the hybridization experiments were carried out in the same manner as that described for nitrocellulose. In addition, the probe could be removed from Whatman 541 paper by washing in 0.5 M NaOH for 30 minutes and then washing in 2 ×SSC (1 ×SSC is 0.15 M NaCl plus 0.015 M sodium citrate)-0.1% SDS for 30 minutes; after air drying, hybridization could be repeated as described above.

Hybridization. The solution for prehybridization and hybridization consisted of 50% formamide, 5 ×SSC 0.1% SDS, 1 mM EDTA, and 1×Denhardt solution (0.02% Ficoll, Pharmacia Fine Chemicals, Piscataway, NJ; 0.01% polyvinylpyrrolidone; 0.02% bovine serum albumin). Nitrocellulose filters, prepared as described above, were incubated for 2 to 4 hours in prehybridization solution containing 50 micrograms of heat-denatured, sonicated salmon sperm DNA per ml. The filters were then transferred to fresh hybridization solution containing labeled probe DNA ($10^6$ cpm) and 50 micrograms of heat-denatured, sonicated salmon sperm DNA per ml. The probe DNA was denatured with alkali as described by Hill and Payne, (Hill, W. E., and W. L. Payne, 1984. Genetic methods for the detection of microbial pathogens. Identification of enterotoxigenic *Escherichia coli* by DNA colony hybridization:-collaborative study, J. Assoc. Off. Anal. Chem. 67:801–807) or by boiling for 10 minutes. The filters were hybridized overnight at 37° C.. Excess hybridization mixture was removed, and the filters were washed once in 5×SSC-0.1% SDS at room temperature for 15 minutes, then three times in 2×SSC-0.1% SDS at 65° C. for 15 minutes each, and finally three times in 0.1 x SSC-0.1% SDS at 65° C. for 15 minutes each. Hybridized filters were air dried, and autoradiograms were exposed for 4 to 18 hours at −80° C. with Kodak XAR film and regular intensifying screens.

As a part of the plasmid mapping studies, the Southern blot hybridization technique (Southern, E. M., 1975. Detection of specific sequences among DNA fragments separated by gel electrophoresis, J. Mol. Biol. 98:503–517) was used to transfer DNA from an agarose gel onto a nitrocellulose filter in 6 x SSC. Probe hybridization to the Southern blots was carried out as described by Maniatis, et al. (Maniatis, T., E. F. Fritsch, and J. Sambrook, 1982. Molecular cloning. A laboratory manual, Cold Spring Harbor Laboratory, Cold Spring Harbor, NY).

Studies of probe hybridization sensitivity. A minifold II apparatus (Schleicher & Schuell) was used to deposit 10-fold dilutions of overnight bacterial cultures onto nitrocellulose filters. We prepared dilutions in 0.9% saline and plated them on nutrient agar to obtain viable counts. These filters were processed and hybridized in the same manner as for colony hybridization studies, as described above. In an attempt to increase sensitivity, 10% dextran sulfate or increased amounts of probe DNA ($10^7$ to 108 total cpm) or both were added to the hybridization mixture in some experiments. Kodak XAR film was exposed at −80° C. for various times from 18 to 72 hours.

Construction of DNA Probes Specific for Vi Antigen Structural genes

Utilizing basic genetic and epidemiological data obtained over the past 50 years or so on Vi antigen organization and the absolute correlation of the Vi antigen with all strains of *S. typhi*, we decided to develop a rapid detection system for *S. typhi* using a DNA hybridization assay and a DNA probe specific for the Vi gene re9ion. In a previous study, chromosomal DNA from *E. coli* WR2376, which contained the chromosomally integrated C. freundii WR7004 genes encoding Mel$^{30}$ (melibiose utilization) and the adjacent Vi antigen structural genes (i.e., the viaB locus), was partially digested with endonuclease PstI and the resulting material was cosmid cloned into the vector plasmid pHC79. One recombinant cosmid, pWR75, contained a 31-kb insert and expressed both tetracycline resistance and the Vi antigen in *E. coli* HB101, which normally contains functional viaA sequences, Baron, L. S., D. J. Kopecko, S. M. McCowen, N. J. Snellings, E. M. Johnson, W. C. Reid, and C. A. Life, 1982, Genetic and molecular studies on the regulation of atypical citrate utilization and variable Vi antigen expression in enteric bacteria, pages 175-194. In Hollaender (Editor), Genetic engineering of microorganisms for chemicals, Plenum Press, NY. In further studies aimed at investigating the reversible nature of Vi antigen expression, we subcloned Vi antigen genes from pWR75 into the single-copy plasmid pDPT429 by using a partial EcoRl digest of both plasmids. One resulting recombinant plasmid, pWR80, was isolated, which has a 29-kb fragment from pWR75 inserted into pDPT429 (Baron, et al., Abstr. Annu. Meet. Am. Soc. Microbiol., 1983). We used Vi antigen-expressing plasmid pWR80 as our beginning material to identify and study potential Vi gene-specific DNA probes. Initially, we reduced the insert by partially digesting pWR80 with EcoRl and inserting an 18-kb fragment into the EcoR1 site of the broad-host-range vector pRK290 to generate pWR122, a Vi antigen-expressing recombinant plasmid. This 18-kb viaB DNA insert in pWR122 consists of two EcoRl fragments, which we designated EcoR1-A and EcoR1-B (8.6 and 9.4 kb, respectively). Since vector pRK290 was derived from Pseudomonas sp., Ditta, G., S. Stanfield, D. Corbin, and D. R. Helinski, 1980, Broad host range DNA cloning system for gram-negative bacteria; construction of a gene bank of *Rhizobium meliloti.* Proc. Natl. Acad. Sci, U.S.A. 77:7347-7351, it was hoped that this vector would not share homology with enteric bacteria. HoweYer, when $^{32}$P-labeled pWR122 was used as a probe, it hybridized weakly to DNAs of some *E. coli* and *Shigella* strains, and further cloning of the insert was necessary. The 18-kb viaB insert of pWR122 was then cloned into pACKCl (a small, amplifiable ColEl derivative vector) by ligation of EcoR1-digested pWR122 and pACKCl, resulting in the construction of a Vi antigen-expressing recombinant plasmid, pWR127. We separately subcloned EcoR1-A and EcoR1-B, the two fragments of the viaB region, into the vectors pBR325 and pACKCl, respectively, to construct pWR141 and pWR137. Cells harboring plasmids pWR137 or pWR141 do not express the Vi antigen. In all of the cloning studies, we assessed Vi antigen expression by using the three methods described above. Before further subdividing these two viaB gene fragments, we attempted to assess their hybridization specificity.

Our method for the detection of *Salmonella typhi* and other related bacteria capable of expressing the Vi antigen comprises, allowing a clinical specimen of the bacteria to react with a DNA probe, consisting of the ViaB portion of the DNA regions encoding the Vi antigen, in a DNA hybridization reaction with the clinical specimen. The DNA probe used in our method is typically a linear DNA fragment, having a molecular size equal to or less than 18,000 nucleotide base pairs, containing the ViaB gene sequences of *Citrobacter freundii, Salmonella typhi,* or other related enteric bacteria expressing the Vi antigen. It should be noted that virtually any plasmid vector could h=used to clone the Vi antigen gene sequences. The use of those vectors described above and listed in Table 3 are illustrative were selected for the convenience of applicants without any implied limitation on the practice of this invention. Also, one could isolate Vi gene specific sequences from either *S. typhi, S. paratyphi* C, or other rare isolates of Vi antigen-expressing enteric bacteria. We used *C. freundii* as a source of the Vi genes because of the experimental ease of this system. Alternatively, one could synthesize an oligonucleotide probe based on the specific DNA sequences within the 18 kb ViaB gene segment described above.

Testing of Vi DNA Probe for Specificity

The DNA of plasmids pWR80, pWR122, and the vector pRK290 was radiolabelled with 32P by the conventional nick translation procedure (Maniatis, T., et al., 1982, Molecular Cloning - A Laboratory Manual, Cold Spring Harbor Labs., NY). Cells of tester bacterial strains were implanted onto nitrocellulose filter paper. The loaded test filters with positive and negative experimental control spots were reacted by standard DNA filter hybridization reactions (Maniatis, T., et al., 1982, Molecular Cloning—A Laboratory Manual, Cold Spring Harbor Labs., NY, see Table 1) to each above radiolabeled DNA probe. Finally, the hybridized filters were exposed to X-ray film to detect positive hybridization reactions. The results shown in Table 2 were obtained. Whole plasmid probe pWR80, containing 29 kilobases of Citrobacter DNA, reacted with the appropriate ViaB+control strains but also reacted undesirably and strongly with many Shigella strains. Next, the recombinant plasmid pWR122 (consisting of pRK290 plus 18 kb of ViaB gene sequences) was tested and proved to be a good hybridization probe. pWR122 reacted strongly with all Vi+control strains, did not react with several control Vi−Salmonella typhimurium strains, and showed differentially (i.e. can distinguish from a strong reaction) minor reaction, with certain Shigella strains. Further studies (Table 2) showed that the pRK290 plasmid vector probe alone reacted slightly with these same Shigella strains. This result was unexpected since pRK290 is a Pseudomonas plasmid and was thought to have no homology to typical enteric bacterial strains. However, these latter data convincingly demonstrate that the ViaB gene sequences in pWR122 are hybridizing strongly with the analogous ViaB sequences in the tester bacteria and that the slight reaction between the pWR122 probe and certain Shigella strains is due to the pRK290 vector sequences. Thus, pRK290 can not be used together with the ViaB gene sequences as a whole plasmid probe.

To circumvent this slight crossreaction, we assayed the EcoR1-A and EcoR1-B restriction fragments of the cloned ViaB gene sequences of pWR122 for their potential use as a highly specific DNA probe. Colony hybridization experiments, as described above, were conducted to determine if either the EcoR1-A or EcoR1-B fragments of the viaB region could be used as hybridization probes for detecting the presence of the Vi gene locus in the test bacterial strains. Bacterial DNA was fixed on nitrocellulose filters and probed with $^{32}$P-labeled DNA as described above. Several positive and negative controls were included on each filter. *C. freundii* WR7004, from which the probe Vi antigen genes were originally cloned, served as one positive control. *S. typhi* WR4201 was always included as a typical Vi antigen-expressing typhoid strain. *S. typhi* WR4205 contains a mutation in the viaA region but has an intact viaB locus. It, therefore, was used as a positive control for the presence of Vi structural genes in *S. typhi*. However, *S. typhi* WR4226 contains an intact viaA region, but the viaB locus has been replaced by *S. typhimurium* chromosomal DNA; this created a ViaB−− phenotype, and thus, strain WR4226 served as a negative *S. typhi* control. The Vi-positive *E. coli* WR2376, (Baron, L. S., D. J. Kopecko, S. M. McCowen, N. J. Snellings, E. M. Johnson, W. C. Reid, and C. A. Life, 1982, Genetic and molecular studies on the regulation of atypical citrate utilization and variable Vi antigen expression in enteric bacteria, pages 175-194. In Hollaender (edition), Genetic engineering of microorganisms for chemicals, Plenum Press, NY) was used as another positive control. Strain 17-59 is a rare, Vi-positive isolate of *S. dublin* and was used as an additional positive control, (LeMinor, L., and P. Nicolle, 1964, Sur deux souches de *Salmonella dublin* possedant l'antigen Vi. Ann. Inst. Pasteur (Paris) 107:550-556). A representative sample of various enteric bacterial strains (e.g.,*E. coli, S. typhimurium, S. sonnei,* and *S. flexneri*) was used to test the specificity of the various probes. Table 4 summarizes the results of these studies.

Both EcoR1-A and EcoR1-B were tested as hybridization probes with nitrocellulose filters as well as Whatman 541 paper. The EcoRI-A probe only hybridized with DNA samples containing the viaB locus, whether or not the Vi antigen was expressed (Table 4). Of 140 various Salmonella strains (Table 4) obtained from the CDC, the EcoR1-A probe hybridized only to DNA from colonies of *S. typhi, S. paratyphi* C, and Vi-positive *S. dublin,* as one would expect of a highly specific probe. No hybridization of EcoR1-A was detected against DNA from 16 Citrobacter strains obtained from the CDC.

The EcoR1-B probe was less specific. Although EcoR1-B hybridized strongly to DNA samples containing the viaB locus, a weak hybridization signal was detected against many Salmonella and Citrobacter strains. Furthermore, an unexpected strong hybridization of EcoR1-B to Citrobacter strain 4182-83 was observed.

In recently reported hybridization experiments, cloned K1 capsular antigen genes exhibited homology with DNA from strains of *E. coli* capsular types K92, K7, and K100, (Echarti, C., B. Hirschel, G. J. Boulnois, J. M. Varley, F. Waldv ©9el, and K. N. Timmis, 1983, Cloning and analysis of the K1 capsule biosynthesis genes of *Escherichia coli*; lack of homology with *Neisseria meningitidis* group B DNA sequences, Infect. Immun. 41:54–60). Therefore, we probed several *E. coli* strains that produce capsular antigens with EcoR1-A and EcoR1-B to see if any hybridization could be detected. After hybridization of Whatman 541 paper, autoradiograms resulting from a 4-hour exposure were identical when EcoR1-A or EcoR1-B was used as a probe. Strong hybridization was observed with DNA from positive control strains with viaB sequences, but hybridization was not detected against the other strains tested, which included negative controls and strains of *E. coli* that produce common capsular antigens. Although hybridization with EcoR1-A was not detected even with longer exposure, weak hybridization between EcoR1-B and these *E. coli* strains was observed when the filters were autoradiographed overnight. Thus, one example of an operable subset of the cloned 18 kb ViaB region is the 8.6 kb EcoR1-A fragment made by us and shown here to serve as an absolutely specific probe.

Restriction mapping of EcoR1-A. Since the EcoR1-A Fragment of the viaB gene region appeared to serve as a highly specific DNA probe, we decided to map its sites for endonuclease cleavage with several restriction enzymes. Plasmid pWR141 contains the EcoR1-A of pWR127 incorporated into pBR325. Single and double restriction endonuclease digests of pWR141 were resolved by electrophoresis on agarose gels, and we analyzed the DNA fragments by size and Southern blot hybridization to construct a restriction map (FIG. 1).

Study of probe sensitivity. To determine the fewest number of bacteria that could be detected with the EcoR1-A probe and the radiolabeling procedure, we performed the following study. The DNA from $10^1$ to $10^5$ cells of each of three test bacterial strains was fixed on a nitrocellulose filter and probed with EcoR1-A. When dextran sulfate and additional probe ($10^7$ $10^8$ cpm) were used in the hybridization mixture, $10^3$ Vi-positive cells could be clearly detected (Table 5). In some experiments, as few as 100 to 500 Vi-positive cells were detected, but detection was made difficult because of increased nonspecific reactivity.

CONCLUSION

Rapid identification tests for microbial pathogens are currently being developed by recombinant DNA technology combined with radio- or enzyme-linked immunoassay techniques. DNA probe detection systems have been reported for the following enteric bacteria:enterotoxigenic *E. coli* (Hill, W. E., and W. L. Payne, 1984, Genetic methods for the detection of microbial pathogens, Identification of enterotoxigenic *Escherichia coli* by DNA colony hybridizaion: collaborative study, J. Assoc. Off. Anal. Chem. 67:801–807; Moseley, S. L., P. Echeverria, J. Seriwatana, C. Tirapat, W. Chiacumpa, T. Sakuldaipeara, and S. Falkow, 1982, Identification of enterotoxigenic *Escherichia coli* by colony hybridization using three enterotoxin gene probes, J. Infect. Dis. 145:863–869; Vibrio spp., Kaper, J. B., R. K. Campen, R. J. Seidler, M. M. Baldini, and S. Falkow, 1984, Cloning of the thermostable direct or Kanagawa phenomenon-associated hemolysin of *Vibrio parahaemolyticus*, Infect. Immun. 45:290–292; Kaper, J. B., and M. M. Levine, 1981, Cloned cholera enterotoxin genes in study and prevention of cholera, Lancet, ii:1162–1164; *Yersinia enterocolitica*, Hill, W. E., W. L. Payne, and C. C. G. Aulisio, 1983, Detection and enumeration of virulent *Yersinia enterocolitica* in food by DNA colony hybridization, Appl. Environ. Microbiol. 46:636–641; Salmonella spp., Fitts, R., M. Diamond, C. Hamilton, and M. Neri, 1983, DNA-DNA hybridization assay for detection of Salmonella spp. in foods, Appl. Environ. Microbiol. 46:1146–1151; and Shigella spp. Boileau, C. R., H. M. d'Hauteville, and P. J. Sansonetti, 1984, DNA hybridization technique to detect Shigella species and enteroinvasive *Escherichia coli*, J. Clin. Microbiol. 20:959–961).

Typhoid fever remains a serious public health problem in developing countries and continues to be endemic in many areas of the world. Currently, microbiological identification of *S. typhi* from clinical specimens generally requires 36 to 48 hours. To simplify identification, we assessed the Vi capsular antigen ViaB structural gene region for use in the development of a rapid detection DNA probe system for *S. typhi*.

We have provided sufficient detailed disclosure to enable one skilled in the art to make the viaB gene probe. Either *S. typhi, C freundii* or any other Vi-antigen expressing enteric bacterium could be used as a source of the viaB gene region. As discussed herein, chromosomal DNA containing the viaB gene region was cleaved with the Pst 1 restriction endonuclease and inserted into the cosmid cloning vector pHC79 by standard cloning techniques (see Maniatis, T , et al., 1982. Molecular cloning - a laboratory Manual, Cold Spring Harbor Labs., NY). *E. coli* C600 mel−recipient cells infected with the recombinant cosmids generated above were examined and several Mel+, Vi antigenexpressing clones were isolated Techniques for testing the melibiose character and ensuring Vi antigen expression are clearly presented in the Snellings article (J. Bacteriol. 145:1010–1017, 1981) which describes procedures for testing Vi antigen expression. The cloned viaB genes were reduced in size from 31 kb to 18 kb and eventually to 8.6kb by the subcloning procedures described herein. Although the information presented by us in the specification is enabling to one skilled in the art to make a probe according to this invention, the 18 kb DNA probe defined in the specification has been deposited in the ATCC and designated WR3007, which is *Escherichia coli* HB101 (pWR122), having the assigned ATCC No. 67096. Additionally, the experiments conducted to test probe specificity have been discussed herein and the results are summarized in Tables 2 and 4. The pWR80 is a recombinant plasmid containing 29 kilobase pairs of inserted DNA including the viaB gene region of *C. freundii.* When pWR80 was used as a probe, it cross-reacted with some bacterial strains that did not contain the Vi antigen genes (see Table 2 under column for pWP80). Thus, it was unsuitable as a specific probe. However, recombinant plasmid pWR122 consists of the vector plasmid pRK290 containing the 18 kilobase pair DNA insert including the ViaB gene region and this plasmid reacts strongly only with bacteria containing Vi antigen genes. Unfortunately, pWR122 reacted very weakly and nonspecifically with several Shigella strains. However, as shown in the right hand column of Table 2, the vector plasmid pRK290 alone reacts weakly and nonspecifically with these same Shigella strains. These data convincingly demonstrate that the weak, nonspecific reaction of the recombinant plasmid pWR122 with Shigella strains is due entirely to the pRK290 vector component of pWR122. In other words, the 18 kilobase pair region cloned into plasmid vector pRK290 to form recombinant plasmid pWR122 is specific for bacteria carrying the viaB gene region, as demonstrated in Table 2. Thus, these data show that the viaB gene region probe of 18 kilobase pairs in length will serve as a specific probe for diagnostic detection of enteric bacteria expressing the Vi antigen (i.e. mainly S. typhi). As disclosed herein, the viaB gene region fragments must be separated from pRK290 in order to be used as a specific probe, i.e. to differentiate only those organisms expressing the Vi antigen. It should be noted that hybridization strength is discussed in the legend to Table 2. A strong hybridization reaction (4+) can be easily distinguished visually from a weak (1+) reaction (i.e. the stronger hybridization reaction gives a more intense color signal; a 4+ reaction would generate an intense dark spot whereas a 1+ reaction would generate a very light grey shading). Also, it should be realized that no available diagnostic probes are 100% specific, but at times give up to 5% false positive crossreaction. One to five percent crossreaction is an acceptable level of nonspecificity for most purposes. Thus, weak crossreaction of a probe does not eliminate the practical usefulness of a DNA segment as a diagnostic probe. The 18 kb probe is itself and the 8.6 kb fragment thereof are considered to be specific for bacteria carrying viaB gene sequences and serve as useful diagnostic probes. Since the 8.6 kilobase EcoR1-A fragment has been shown to act as an absolutely specific nucleic acid hybridization probe, any subset of sequences within this region will be highly specific for the ViaB gene region. Similarly, any subset of sequences within the larger cloned 18 kilobase viaB region will also serve as a differentially specific probe. Current nucleic acid hybridizaion reactions require a nucleic probe of a minimum size of approximately 10 nucleic acid base pairs. Thus, any subset sequence from about 10 base pairs to 18 kilobase pair of the cloned viaB region will be used as a specific nucleic acid probe in accordance with this invention. We consider our disclosure to be sufficiently enabling to allow on skilled in the art to construct a similar probe and to use the 18 kb probe in standard hybridization reactions (pages 387 to 389 of the Maniatis Molecular Cloning Manual or U. S. Pat. No. 4,358,535, describe readily available techniques) for detecting Vi antigen expressing enteric bacteria.

Our approach for development of the DNA probe for the detection of S. typhi involved cloning the viaB region of C. freundii. The smallest recombinant clone that expresses the Vi antigen contained an 18-kb DNA insert. Digestion of this 18-kb cloned insert with EcoR1 restriction endonuclease produced two fragments, which were designated as EcoR1-A (8.6 kb) and EcoR1-B (9.4 kb). Each of these fragments was tested as a possible probe for detecting S. typhi. When used to probe a variety of enteric strains, including highly related Salmonella and Citrobacter strains, EcoR1-B was not absolutely specific. Weak hybridization of EcoR1-B was observed with many Salmonella strains, some Citrobacter strains, and E. coli strains producing capsular antigens. EcoR1-A, however, was absolutely specific for strains containing viaB gene sequences and is considered to be a highly specific DNA probe for rapid diagnostic detection of S. typhi.

Using various enteric bacterial strains, we tested probe specificity with nitrocellulose and Whatman 541 paper and found Whatman 541 paper to have several advantages when used in the colony hybridization protocol. As a paper with high wet strength, it is easier to handle than nitrocellulose. In addition, the papers do not have to be baked in a vacuum oven to fix DNA to the solid support. Another advantage of Whatman 541 paper is that prehybridization is not necessary (S. Moseley, personal communication). Finally, hybridized probe can be removed easily and the samples can be tested sequentially with different probes.

In sensitivity studies, the EcoR1-A probe detected $10^4$ Vi-expressing cells with the standard hybridization solution as described above. Since dextran sulfate has been shown to increase sensitivity (Totten, P. A., K. K. Holmes, H. H. Handsfield, J. S. Knapp, P. L. Perine, and S. Falkow, 1983, DNA hybridization technique for the detection of Neisseria gonorrhoeae in men with urethritis, J. Infect. Dis. 148:462–471; Wahl, G. M., M. Stern, and G. R. Stark, 1979, Efficient transfer of large DNA fragments from agarose gels to diazonbenzyloxymethyl-paper and rapid hybridization by using dextran sulfate, Proc. Natl. Acad. Sci. U.S.A. 76:3683–3687) we reexamined the sensitivity of our probe with this reagent included in the hybridization solution. A 10-fold increase in sensitivity was observed when added (Table 4). We expect that the EcoR1-A probe can be placed into a nonradioactive labeled system in which detector signals can be amplified, resulting in a further increase in sensitivity as well as rapid identification of S. typhi.

TABLE 1

| Outline of General Method for Genetic Identification of Pathogens | | |
|---|---|---|
| A. Preparation of DNA probe | B. Preparation of Clinical Specimen | C. Colony Hybridization |
| 1. Growth of bacteria | Grow bacterial cultures or isolate specimens | Pre-incubate filters to eliminate nonspecific hybridization |
| 2. Amplify plasmid | Inoculation of above culture or specimen on filter or other support material | DNA Hybridization reaction |
| 3. Label DNA fragment | Lyse colonies and fix (i.e. single stranded DNA to the support material such as nitrocellulose filter) | Wash filters thoroughly |
| 4. Purify plasmid | | Detection of bound probe nucleic acid |
| 5. Digest plasmid with restriction endonculeases | | Interpretation |

TABLE 1-continued

| Outline of General Method for Genetic Identification of Pathogens | | |
|---|---|---|
| A. Preparation of DNA probe | B. Preparation of Clinical Specimen | C. Colony Hybridization |
| 6. Purify labelled DNA probe fragment | | |

TABLE 2

Testing of Vi DNA Probes for Specificity

| Bacterial Source[a] | ViaB gene region presence[b] | Hybridization reactions obtained with probes | | |
|---|---|---|---|---|
| | | pWR80 | pWR122 | pRK290 |
| *Citrobacter freundii* 7004 | + | 4+ | 4+ | — |
| *Citrobacter freundii* 7011 | + | 4+ | 4+ | — |
| *Salmonella typhi* 643 | + | 3+ | 3+ | — |
| *Salmonella typhi* 643 W | + | 3+ | 3+ | — |
| *Salmonella typhi* 643 viaB− | — | — | — | N.D. |
| *Escherichia coli* C600 viaB+ | + | 3+ | 3+ | N.D. |
| *Salmonella typhimurium* C-5 | — | — | — | N.D. |
| *Salmonella typhimurium* TML | — | — | — | N.D. |
| *Salmonella typhimurium* Fisher | — | — | — | N.D. |
| *Shigella sonnei* form I | — | 4+ | + | N.D. |
| *Shigella sonnei* form II | — | 4+ | + | + |
| *Shigella flexneri* M25-8A | — | + | + | + |
| *Shigella flexneri* M42-43 | — | 4+ | + | + |
| *Shigella flexneri* serotype 3 | — | 4+ | + | + |
| *Shigella flexneri* serotype 4 | — | 4+ | + | N.D. |
| *Shigella flexneri* serotype 5 | — | 4+ | + | + |
| *Shigella flexneri* serotype 6 | — | 4+ | + | N.D. |
| *Escherichia coli* AB313 | — | + | + | + |
| *Escherichia coli* HB101 (pRK290) | — | N.D. | N.D. | 4+ |

[a] Cells of each bacterial source were spotted on nitrocellulose filters and hybridized with one of the three indicated probes.
[b] (+) indicates presence of ViaB gene region and (−) indicates absence of this DNA region.
c. Strength of hybridization reactions was measured by autoradiography. (4+) = highly positive, (−) = negative. N.D. = not determined.

TABLE 3

Plasmid Cloning Vectors

| Plasmid | Size (kb) | Relevant characteristics[a] | Source |
|---|---|---|---|
| pHC79 | 6.5 | Ap$^r$ (PstI), Tc$^r$ | B. Hohn[e] |
| pDPT429[b] | 8.7 | Cm$^r$ (EcoRI), Sp$^r$ | D. Taylor[c] |
| pRK290 | 20.0 | Tc$^r$ (EcoRI) | D. Helinski[f] |
| pACKCl | 4.0 | Cm$^r$ (EcoRI), Km$^r$ | V. Burdett[d] |
| pBR325 | 6.0 | Cm$^r$ (EcoRI), Ap$^r$, Tc$^r$ | F. Bolivar[g] |

[a] Single restriction sites that inactivate drug resistance in the vectors are included in parentheses next to the appropriate antibiotic resistance. Ar$^r$, ampicillin resistant; Tc$^r$, tetracycline resistant; Cm$^r$, chloramphenicol resistant; Sp$^r$, spectinomycin resistant; and Km$^r$, kanamycin resistant.
[b] Single-copy vector derived from plasmid R100.
[c] SmithKline Beckman Corp., Philadelphia, PA.
[d] Duke University, Durham, NC.
[e] B. Hohn and J. Collins, 1980, A small cosmid for efficient cloning of large DNA fragments, Gene, 11:291-298.
[f] G. Ditta, S. Stanfield, D. Corgin, and D. R. Helinski, 1980, Broad host range DNA cloning system for gram-negative bacteria; construction of a gene bank of *Rhizobium meliloti*. Proc. Natl. Acad. Sci. U.S.A., 77:7347-7351.
[g] F. Bolivar, 1978, Construction and characterization of new cloning vehicles, III, Derivatives of plasmid pBR322 carrying unique EcoRI generated recombinant molecules, Gene, 4:121-136.

TABLE 4

Summary of in situ Colony Hybridization Experiments

| Bacterial species | Strains tested | Source | Response to probe:[a] | |
|---|---|---|---|---|
| | | | EcoRI-A | EcoRI-B |
| *C. freundii* | WR7004 Vi+ | WRAIR | ++++ | ++++ |
| *C. freundii* | 4182-83 | CDC | — | +++ |
| *C. freundii* | Five strains | CDC | — | — |
| *C. diversus* | Five strains | CDC | — | + |
| *C. amalonaticus* | Five strains | CDC | — | + |
| *S. typhi* | WR4201 (ViaA+ ViaB+) | WRAIR | ++++ | ++++ |
| *S. typhi* | WR4205 (ViaA− ViaB+) | WRAIR | ++++ | ++++ |
| *S. typhi* | WR4226 (ViaA+ ViaB−) | WRAIR | — | — |
| *S. typhi* | Ty 2 | WRAIR | ++++ | ++++ |
| *S. typhi* | Six strains | CDC | ++++ | ++++ |
| *S. paratyphi* C | Two strains | CDC | ++++ | ++++ |
| *S. dublin* Vi+ | 17-59 and a CDC strain | L. LeMinor | ++++ | ++++ |
| *S. typhimurium* | C-5 | WRAIR | — | — |
| | TML | WRAIR | — | — |
| | CDC strain | CDC | — | — |
| Salmonella spp. | 130 CDC strains[b] | CDC | — | +[c] |
| *E. coli* K-12 | AB313 | E. Adelberg | — | — |
| | HB101 | H. Boyer | — | — |
| | 52 R137 (LT+) | WRAIR | — | — |
| *E. coli* | 218 (O18:K1) | R. Silver | — | + |
| | 437 (O4:K12) | R. Silver | — | + |
| | 439 (K92) | R. Silver | — | + |
| | 440 (O86:K2) | R. Silver | — | + |
| | 441 (O15:K7) | R. Silver | — | + |
| | 442 (K15) | R. Silver | — | + |
| | 501 (O75:K100) | R. Silver | — | + |
| *S. flexneri* | Serotype 1b, M25-8A | WRAIR | — | — |
| | Serotype 2a, M4243 | WRAIR | — | — |
| | Serotype 3, J17B | WRAIR | — | — |
| | Serotype 4, Willis | WRAIR | — | — |
| | Serotype 5, M90T | WRAIR | — | — |
| | Serotype 6, CCH060 | WRAIR | — | — |
| *S. sonnei* | 53G form I | WRAIR | — | — |

TABLE 4-continued

Summary of in situ Colony Hyridization Experiments

| Bacterial species | Strains tested | Source | Response to probe:[a] | |
|---|---|---|---|---|
| | | | EcoRI-A | EcoRI-B |
| | 53G form II | WRAIR | − | − |

[a]++++, Very strong hybridization; +++, strong hybridization; +, weak hybridization; −, no hybridization observed.
[b]Hybridization data in this row exclude the following CDC strains; *S. typhi, S. paratyphi* C, and *S. dublin* Vi+.
[c]Weak hybridization was detected in 27% of Salmonella strains probed with the EcoRI-B.

TABLE 5

| | Sensitivity of EcoRI-A Probe | | |
|---|---|---|---|
| | Hybridization reaction with:[a] | | |
| No. of bacterial cells | C. freundii WR7004 | E. coli HB101 | S. typhi WR4201 |
| $10^5$ | ++++ | − | ++++ |
| $10^4$ | ++ | − | ++ |
| $10^3$ | + | − | + |
| $10^2$ | −(+)[b] | −. | −(+)[b] |
| $10^1$ | − | − | − |

[a]Hybridication observed with addition of dextran sulfate and probe DNA ($10^7$ cpm) to the hybridization mixture.
[b]In some experiments with probe DNA ($10^8$ cpm), as few as 100 to 500 cells could be detected.

We claim:

1. A method for detecting enteric bacteria containing a nucleic acid region designated viaB and capable of expressing Vi antigen, comprising:
   (a) lysing bacteria in a clinical specimen and denaturing DNA contained therein;
   (b) fixing the denatured DNA to a support material;
   (c) contacting the denatured DNA of step b with a nucleic acid probe under conditions to permit hybridization of the probe with complementary sequences in the denatured DNA, wherein the nucleic acid probe is about 8,600 to about 18,000 nucleotide bases or base pairs inn size and contains a nucleotide sequence complementary to the EcoR1-A fragment of the viaB nucleic acid region which encodes the VVi antigen; and
   (d) detecting the presence of enteric bacteria in the clinical specimen by detecting hybridized probe on the support material.

2. The method of claim 1 wherein the nucleic acid probe contains the viaB nucleic acid region of *Citrobacter freundii, Salmonella paratyphi* C or *Salmonella typhi*.

3. The method of claim 1 wherein the nucleic acid probe contains the viaB nucleic acid region of *Citrobacter freundii*.

4. The method of claim 1 wherein the nucleic acid probe contains the viaB nucleic acid region of *Salmonella paratyphi* C.

5. The method of claim 1 wherein the nucleic acid probe contains the viaB nucleic acid region of *Salmonella typhi*.

6. The method of claim 1 wherein the nucleic acid probe is about 18,000 nucleotide bases or base pairs in size.

7. The method of claim 6 wherein the nucleic acid probe is contained in the recombinant plasmid WR122 carried in the strain *Escherichia coli* HB101 (ATCC 67096).

8. The method of claim 1 wherein the nucleic acid probe is about 8,600 bases or base pairs in size.

9. The method of claim 1 wherein the clinical specimen comprises blood or fecal material, the support material is nitrocellulose, and the nucleic acid probe is radiolabeled.

10. The method of claim 9 wherein hybridized probe on the nitrocellulose is detected by autoradiography.

11. The method of claim 1 wherein the nucleic acid probe is labelled with an immunologically detectable nucleotide analog.

12. The method of claim 11 wherein the immunologically detectable nucleotide analog is a biotinylated nucleotide derivative.

13. The method of claim 1 wherein the nucleic acid probe is labeled by a nonradiolabeling procedure.

14. A nucleic acid hybridization probe consisting of about 8,600 to about 18,000 nucleotide bases or base pairs and containing a nucleotide sequence complementary to the EcoR10A fragment of the viaB nucleic acid region which encodes the Vi antigen.

15. The nucleic acid probe of claim 14 wherein the probe contains the viaB nucleic acid region of *Citrobacter freundii, Salmonella paratyphi* C or *Salmonella typhi*.

16. The nucleic acid probe of claim 14 wherein the probe contains the viaB nucleic acid region of *Citrobacter freundii*.

17. The nucleic acid probe of claim 14 wherein the probe contains the viaB nucleic acid region of *Salmonella paratyphi* C.

18. The nucleic acid probe of claim 14 wherein the probe contains the viaB nucleic acid region of *Salmonella typhi*.

19. The nucleic acid probe of claim 14 wherein the probe is about 18,000 nucleotide bases or base pairs in size.

20. The nucleic acid probe of claim 14 wherein the probe is contained in the recombinant plasmid WR 122 carried in the strain *Escherichia coli* HB 101 (ATCC 67096).

21. The linear nucleic acid probe of claim 14 wherein the probe is about 8,600 nucleotide bases or base pairs in size.

* * * * *